US010968428B2

(12) United States Patent
Nishida et al.

(10) Patent No.: US 10,968,428 B2
(45) Date of Patent: Apr. 6, 2021

(54) CORNEAL ENDOTHELIAL CELL MARKER

(71) Applicant: OSAKA UNIVERSITY, Osaka (JP)

(72) Inventors: Kohji Nishida, Osaka (JP); Motokazu Tsujikawa, Osaka (JP); Susumu Hara, Osaka (JP); Satoshi Kawasaki, Osaka (JP); Masahito Yoshihara, Saitama (JP); Masayoshi Itoh, Saitama (JP); Hideya Kawaji, Saitama (JP); Hiroko Ohmiya, Saitama (JP)

(73) Assignee: OSAKA UNIVERSITY, Osaka (JP)

( * ) Notice: Subject to any disclaimer, the term of this patent is extended or adjusted under 35 U.S.C. 154(b) by 135 days.

(21) Appl. No.: 15/508,749

(22) Filed: Mar. 3, 2017

(65) Prior Publication Data
US 2017/0253855 A1 Sep. 7, 2017

Related U.S. Application Data

(63) Continuation-in-part of application No. PCT/JP2015/075164, filed on Sep. 4, 2015.

(30) Foreign Application Priority Data

Sep. 5, 2014 (JP) ................................. 2014-180985

(51) Int. Cl.
*C12N 5/079* (2010.01)
*C12Q 1/68* (2018.01)
(Continued)

(52) U.S. Cl.
CPC ............ *C12N 5/0621* (2013.01); *A61K 35/30* (2013.01); *C12N 5/10* (2013.01); *C12N 15/09* (2013.01);
(Continued)

(58) Field of Classification Search
CPC combination set(s) only.
See application file for complete search history.

(56) References Cited

U.S. PATENT DOCUMENTS 10,017,735 B2 * 7/2018 Tan ...................... C12N 5/0621
2009/0232772 A1 9/2009 Amano et al.
(Continued)

FOREIGN PATENT DOCUMENTS

WO 2006/092894 9/2006
WO 2011/096593 8/2011
(Continued)

OTHER PUBLICATIONS

Parte et al., Detection, Characterization, and Spontaneous Differentiation in Vitro of Very Small Embryonic-Like Putative Stem Cells in Adult Mammalian Ovary, Stem Cells and Development, vol. 20, No. 8, 2011.*
(Continued)

*Primary Examiner* — Sean C. Barron
(74) *Attorney, Agent, or Firm* — Wenderoth, Lind & Ponack, L.L.P.

(57) ABSTRACT

A molecular marker expressed specifically in corneal endothelial cells, and a method for producing one or more corneal endothelial cells using the marker and a method for evaluating one or more corneal endothelial cells using the marker are provided. At least one molecule selected from the group consisting of ZP4, MRGPRX3, GRIP1, GLP1R, HTR1D, and CLRN1 is used as a marker specific to corneal endothelial cells.

5 Claims, 7 Drawing Sheets

Specification includes a Sequence Listing.

(51) Int. Cl.
- C12N 15/09 (2006.01)
- C12N 5/10 (2006.01)
- A61K 35/30 (2015.01)
- C12N 15/10 (2006.01)
- C12N 15/67 (2006.01)
- C12Q 1/686 (2018.01)
- G01N 33/569 (2006.01)
- A61L 27/00 (2006.01)

(52) U.S. Cl.
CPC .......... *C12N 15/10* (2013.01); *C12N 15/67* (2013.01); *C12Q 1/68* (2013.01); *C12Q 1/686* (2013.01); *G01N 33/56966* (2013.01); *A61L 27/00* (2013.01); *G01N 2333/705* (2013.01); *G01N 2333/70596* (2013.01)

(56) References Cited

U.S. PATENT DOCUMENTS

| | | |
|---|---|---|
| 2013/0023050 A1 | 1/2013 | Shima et al. |
| 2014/0170751 A1 | 6/2014 | Hayashi et al. |
| 2014/0315305 A1 | 10/2014 | Shimmura et al. |
| 2015/0202256 A1 | 7/2015 | Nakamura et al. |
| 2016/0257931 A1 | 9/2016 | Shima et al. |
| 2016/0266114 A1* | 9/2016 | Koizumi .............. C12N 5/0621 |

FOREIGN PATENT DOCUMENTS

| | | |
|---|---|---|
| WO | 2013/012087 | 1/2013 |
| WO | 2013/051722 | 4/2013 |
| WO | 2014/007402 | 1/2014 |
| WO | 2015/016371 | 2/2015 |

OTHER PUBLICATIONS

Peh et al., Optimization of human corneal endothelial cell culture: density dependency of successful cultures in vitro, BMC Research Notes 2013, 6:176.*
http://e-immunohistochemistry.info/web/CD117.htm (2008)(last visited May 6, 2019).*
Chen and Duncan. Expression of Steroid Receptor Coactivators in Vertebrate Ocular Tissues. Investigative Ophthalmology & Visual Science (2005), 46, 1877. (Year: 2005).*
Hong et al., "GRIP1, a novel mouse protein that serves as a transcriptional coactivator in yeast for the hormone binding domains of steroid receptors", Proceedings National Academy of Sciences USA, 93:4948-4952 (1996).
Chen et al., "Expression of Steroid Receptor Coactivators in Vertebrate Ocular Tissues", Investigative Ophthalmology & Visual Science, 46: 1877 (2005), Abstract only.
Hasegawa et al., "Amino acid sequence of a porcine zona pellucida glycoprotein ZP4 determined by peptide mapping and cDNA cloning", Journal of Reproduction and Fertility, 100: 245-255 (1994).
Hayashi et al., "Enrichment of corneal epithelial stem/progenitor cells using cell surface markers, integrin $\alpha\alpha_6$ and CD71", Biochem. Biophys. Res. Comm. 367: 256-263 (2008).
Bian et al., "Molecular signatures and biological pathway profiles of human corneal epithelial progenitor cells", The International Journal of Biochemistry & Cell Biology, 42: 1142-1153 (2010).
Kim et al., "Phenotypic characterization of human corneal epithelial cells expanded ex vivo from limbal explant and single cell cultures", Experimental Eye Research, 79: 41-49 (2004).
Cheong et al., "Identification of Cell Surface Markers Glypican-4 and CD200 That Differentiate Human Corneal Endothelium From Stromal Fibroblasts", Investigative Ophthalmology & Visual Science, 54: 4538-4547 (2013).
Extended European Search Report dated Feb. 7, 2018 in European Application No. 15838545.0.
Corrected Extended European Search Report dated Mar. 19, 2018 for European Application No. 15838545.0.

Kanai et al., "Recombinant bovine zona pellucida glycoproteins ZP3 and ZP4 coexpressed in Sf9 cells form a sperm-binding active hetero-complex", The FEBS Journal, 274: 5390-5405 (2007).
Office Action dated May 17, 2018 in Korean Patent Application No. 10-2017-7007769, with English Translation.
Office Action dated Jun. 13, 2017 in corresponding Japanese Application No. 2016-546702, with English Translation.
Kwon et al., "Structure and Expression Analyses of SVA Elements in Relation to Functional Genes", Genomics & Informatics, 11(3):142-148 (2013).
Yoshihara et al., "Discovery of Molecular Markers to Discriminate Corneal Endothelial Cells in the Human Body", PLoS One, 10(3): 1-15 (2015).
The 37th Annual Meeting of the Molecular Biology Society of Japan Koen Yoshishu, 2014, 2P-0115.
Regenerative Medicine, 2014, vol. 13, special extra issue, p. 278, P-1-098.
Journal of Japanese Ophthalmological Society, 2013, vol. 117, special extra issue, p. 378, P-181.
Regenerative Medicine, 2011, vol. 10, special extra issue, p. 163, O-17-1.
Regenerative Medicine, 2010, vol. 9, special extra issue, p. 283, P-081.
Chen et al., "Identification of novel molecular markers through transcriptomic analysis in human fetal and adult corneal endothelial cells", Human Molecular Genetics, 22(7): 1271-1279 (2012).
Ide et al., "Structural characterization of bioengineered human corneal endothelial cell sheets fabricated on temperature-responsive culture dishes", Biomaterials, 27:607-614 (2006).
Joyce, "Proliferative capacity of the corneal endothelium", Progress in Retinal and Eye Research, 22: 359-389 (2003).
Joyce et al., "Potential of human umbilical cord blood mesenchymal stem cells to heal damaged corneal endothelium", Molecular Vision, 18: 547-564 (2012).
Shao et al., "Bone Marrow-Derived Endothelial Progenitor Cells: A Promising Therapeutic Alternative for Corneal Endothelial Dysfunction", Cells Tissues Organs, 193: 253-263 (2011).
Kikuchi et al., "Neural crest-derived multipotent cells in the adult mouse iris stroma", Genes to Cells, 16:273-281 (2011).
Hatou et al., "Functional Corneal Endothelium Derived from Corneal Stroma Stem Cells of Neural Crest Origin by Retinoic Acid and Wnt/β-Catenin Signaling", Stem Cells and Development, 22(5): 828-839 (2013).
Zhang et al., "Isolation and Transplantation of Corneal Endothelial Cell-Like Cells Derived from In-Vitro-Differentiated Human Embryonic Stem Cells", Stem Cells and Development, 23(12): 1340-1354 (2014).
Barry et al., "The Spatial Organization of Corneal Endothelial Cytoskeletal Proteins and Their Relationship to the Apical Junctional Complex", Investigative Ophthalmology & Visual Science, 36(6): 1115-1124 (1995).
Zam et al., "Isolation of the plasma membrane from corneal endothelial cells", Investigative Ophthalmology & Visual Science, 19(6):648-652 (1980).
Vassilev et al., "Loss of N-Cadherin from the Endothelium Causes Stromal Edema and Epithelial Dysgenesis in the Mouse Cornea", Investigative Ophthalmology & Visual Science, 53(11):7183-7193(2012).
Howarth et al., "Detection of the tight junction-associated protein ZO-1 in astrocytes and other nonepithelial cell types", American Journal of Physiology, 262:C461-C469 (1992).
Mobasheri et al., "$Na^+$, $K^+$-ATPase Isozyme Diversity; Comparative Biochemistry and Physiological Implications of Novel Functional Interactions", Bioscience Reports, 20(2):51-91 (2000).
Tsuchiya et al., "Differential expression of N-cadherin and E-cadherin in normal human tissues", Archives of Histology and Cytology, 69(2):135-145 (2006).
Matsui et al., "Derivation of Pluripotential Embryonic Stem Cells from Murine Primordial Germ Cells in Culture", Cell, 70:841-847 (1992).
Resnick et al., "Long-term proliferation of mouse primordial germ cells in culture", Nature, 359:550-551 (1992).

(56) References Cited

OTHER PUBLICATIONS

Kanatsu-Shinohara et al., "Long-Term Proliferation in Culture and Germline Transmission of Mouse Male Germline Stem Cells", Biology of Reproduction, 69:612-616 (2003).

Lee et al., "Derivation of neural crest cells from human pluripotent stem cells", Nature Protocols, 5(4):688-701 (2010).

Hartmann et al., "Early Contact Interactions between Mammalian Gametes In Vitro: Evidence That the Vitellus Influences Adherence between Sperm and Zona Pellucida", Proceedings of the National Academy of Sciences U.S.A., 69(10):2767-2769 (1972).

Gupta et al., "Mammalian zona pellucida glycoproteins: structure and function during fertilization", Cell Tissue Research, 349:665-678 (2012).

Lembo et al., "Proenkephalin A gene products activate a new family of sensory neuron-specific GPCRs", Nature Neuroscience, 5(3):201-209 (2002).

Dong et al., "Characterization of the Glutamate Receptor-Interacting Proteins GRIP1 and GRIP2", The Journal of Neuroscience, 19(16):6930-6941 (1999).

Ørskov, "Glucagon-like peptied-1, a new hormone of the entero-insular axis", Diabetologia, 35:701-711 (1992).

Tornehave et al., "Expression of the GLP-1 Receptor in Mouse, Rat, and Human Pancreas", Journal of Histochemistry & Cytochemistry, 56(9):841-851 (2008).

Harriott et al., "Serotonin type 1D receptors ($5HT_{1d}R$) are differentially distributed in nerve fibres innervating craniofacial tissues", Cephalalgia, 28(9):933-944 (2008).

Kremer et al., "Usher syndrome: molecular links of pathogenesis, proteins and pathways", Human Molecular Genetics, 15(2):R262-R270 (2006).

Geller et al., "CLRN1 is Nonessential in the Mouse Retina but is Required for Cochlear Hair Cell Development", PLoS Genetics, 5(8):1-18 (2009) e1000607.

Ji et al., "δENaC: a novel divergent amiloride-inhibitable sodium channel", American Journal of Physiology Lung Cellular and Molecular Physiology, 303:L1013-L1026 (2012).

Gabow, "Autosomal Dominant Polycystic Kidney Disease", The New England Journal of Medicine, 329(5):332-342 (1993).

Boletta et al., "Role of polycystins in renal tubulogenesis", Trends in Cell Biology, 13(9):484-492 (2003).

Söllner et al., "Snap Receptors implicated in vesicle targeting and fusion", Nature, 362:318-324 (1993).

Gokhale et al., "PPIP5K1 modulates ligand competition between diphosphoinositol polyphosphates and $PtdIns(3,4,5)P_3$ for polyphosphoinositide-binding domains", Biochemical Journal, 453(3):413-426 (2013).

Chen et al., "Identification of novel molecular markers through transcriptomic analysis in human fetal and adult corneal endothelial cells", Human Molecular Genetics, 22(7):1271-1279 (2013).

Trapnell et al., "Differential gene and transcript expression analysis of RNA-seq experiments with TopHat and Cufflinks", Nature Protocols, 7(3):562-578 (2012).

Chng et al., "High throughput Gene Expression Analysis Identifies Reliable Expression Markers of Human Corneal Endothelial Cells", PLoS One, 8(7):1-15 (2013) e67546.

International Search Report, dated Nov. 2, 2015, in corresponding International Application No. PCT/JP2015/075164.

Office Action dated Mar. 30, 2020 in corresponding Chinese Patent Application No. 201580057199.4 with English-language translation.

Bettahi et al., "Genome-Wide Transcriptional Analysis of Differentially Expressed Genes in Diabetic, Healing Corneal Epithelial Cells: Hyperglycemia-Suppressed TGFB3 Expression Contributes to the Delay of Epithelial Wound Healing in Diabetic Corneas," Diabetes, 2014, vol. 63, No. 2, pp. 715-727.

Yokoi et al., "Establishment of Functioning Human Corneal Endothelial Cell Line with High Growth Potential," PLoS One, 2012, vol. 7, No. 1, pp. 1-8.

* cited by examiner

CORNEAL ENDOTHELIAL CELL MARKER

TECHNICAL FIELD

The present invention relates to a molecular marker expressed specifically in corneal endothelial cells, a method for producing corneal endothelial cells using the marker and a method for evaluating corneal endothelial cells using the marker.

BACKGROUND ART

The cornea is the transparent front part of the eyeball. From the anterior, the cornea has a corneal epithelium, a Bowman's membrane, a corneal stroma, a Descemet's membrane, and a corneal endothelium. The corneal epithelium is present at the outermost part of the cornea, and functions as a barrier to protect the cornea from foreign matter, such as dust and bacteria. The Bowman's membrane is thought to function as a base for the corneal epithelium. The corneal stroma is the thickest layer among the three layers (i.e., corneal epithelium, corneal stroma, and corneal endothelium), and maintains the strength of the cornea. The Descemet's membrane is located beneath the corneal stroma, and connects the corneal stroma with the corneal endothelium. The corneal endothelium is a monolayer in which hexagonal corneal endothelial cells are regularly arranged like cobblestones; it plays a critical role in maintaining the transparency of the cornea by preventing, by its barrier and pumping functions, the moisture in the anterior chamber from penetrating into the corneal stroma, while maintaining the fluid balance by draining the moisture in the cornea out to the anterior chamber.

Loss of a significant number of corneal endothelial cells due to cell damage caused by genetic or external factors impairs the functions described above, leading to corneal edema. Severe corneal endothelial dysfunction compromises the maintenance of the transparency of the cornea. If bullous keratopathy develops, marked visual loss may result.

Corneal endothelial cells have a very limited capacity for proliferation in the human body. The most effective, fundamental method to treat severe corneal endothelial dysfunction at the moment is corneal transplantation. In fact, bullous keratopathy is the disease for which corneal transplantation has been most often performed. Although full-thickness cornea transplants have, in the past, been performed for corneal endothelial dysfunction, there are problems such as a chronic donor shortage and transplant rejection. To minimize rejection, a technique has been developed that transplants only a partial tissue containing a corneal endothelium to an eye with a disorder (Descemet's Stripping Automated Endothelial Keratoplasty: DSAEK). However, DSAEK also cannot overcome the donor shortage. Attempts to grow corneal endothelial cells in vitro and use the cells in treatment have also been made (Non-patent Literature 1 and Patent Literature 1 to 3). However, repeated passages cause genetic transformation, leading to loss of their functions (Non-patent Literature 2).

To solve the problems described above, a number of studies have been conducted on induction of corneal endothelial cells from umbilical cord blood-derived mesenchymal stem cells (Non-patent Literature 3), bone marrow-derived cells (Non-patent Literature 4), iris-derived stem cells (Non-patent Literature 5), corneal stroma-derived stem cells (Non-patent Literature 6), embryonic stem cells (Non-patent Literature 7), induced pluripotent stem cells (Patent Literature 4), etc., for the purpose of transplant. However, regardless of the origin of the cells, the thus-obtained cultured cells contain different types of cells in addition to corneal endothelial cells. In these studies, therefore, a marker specific to corneal endothelial cells usable to isolate and evaluate corneal endothelial cells (i.e., its target product) is indispensable.

Currently, proteins, such as ZO-1 (Non-patent Literature 8), $Na^+$—$K^+$-ATPase (Non-patent Literature 9), and N-cadherin (Non-patent Literature 10), are used as corneal endothelial cell markers. These proteins, however, are expressed non-specifically in many other types of cells (Non-patent Literature 11 to 13). Thus, isolation of corneal endothelial cells using these proteins is not expected to give a satisfactory outcome, in particular given the multilineage potential of the stem cells used to induce differentiation into corneal endothelial cells.

CITATION LIST

Patent Literature

Patent Literature 1: WO2006/092894A1
Patent Literature 2: WO2011/096593A1
Patent Literature 3: WO2013/012087A1
Patent Literature 4: WO2013/051722A1

Non-Patent Literature

Non-patent Literature 1: Ide T, Nishida K, Yamato M, Sumide T, Utsumi M, et al. (2006) Structural characterization of bioengineered human corneal endothelial cell sheets fabricated on temperature-responsive culture dishes. Biomaterials 27: 607-614.

Non-patent Literature 2: Joyce N C (2003) Proliferative capacity of the corneal endothelium. Prog Retin Eye Res 22: 359-389.

Non-patent Literature 3: Joyce N C, Harris D L, Markov V, Zhang Z, Saitta B (2012) Potential of human umbilical cord blood mesenchymal stem cells to heal damaged corneal endothelium. Mol Vis 18: 547-564.

Non-patent Literature 4: Shao C, Fu Y, Lu W, Fan X (2011) Bone marrow-derived endothelial progenitor cells: a promising therapeutic alternative for corneal endothelial dysfunction. Cells Tissues Organs 193: 253-263.

Non-patent Literature 5: Kikuchi M, Hayashi R, Kanakubo S, Ogasawara A, Yamato M, et al. (2011) Neural crest-derived multipotent cells in the adult mouse iris stroma. Genes Cells 16: 273-281.

Non-patent Literature 6: Hatou S, Yoshida S, Higa K, Miyashita H, Inagaki E, et al. (2013) Functional corneal endothelium derived from corneal stroma stem cells of neural crest origin by retinoic acid and Wnt/β-catenin signaling. Stem Cells Dev 22: 828-839.

Non-patent Literature 7: Zhang, K, Pang, K, Wu, X. (2014) Isolation and transplantation of corneal endothelial cell-like cells derived from in-vitro-differentiated human embryonic stem cells. Stem cells and development 23: 1340-1354.

Non-patent Literature 8: Barry P A, Petroll W M, Andrews P M, Cavanagh H D, Jester J V. (1995) The spatial organization of corneal endothelial cytoskeletal proteins and their relationship to the apical junctional complex. Invest Ophthalmol Vis Sci 36: 1115-1124.

Non-patent Literature 9: Zam Z S, Cerda J, Polack F M. (1980) Isolation of the plasma membrane from corneal endothelial cells. Invest Ophthalmol Vis Sci 19: 648-652.

Non-patent Literature 10: Vassilev V S, Mandai M, Yonemura S, Takeichi M (2012) Loss of N-cadherin from the endothelium causes stromal edema and epithelial dysgenesis in the mouse cornea. Invest Ophthalmol Vis Sci 53: 7183-7193.

Non-patent Literature 11: Howarth A G, Hughes M R, Stevenson B R (1992) Detection of the tight junction-associated protein ZO-1 in astrocytes and other nonepithelial cell types. Am J Physiol 262: C461-469.

Non-patent Literature 12: Mobasheri A, Avila J, Cozar-Castellano I, Brownleader M D, Trevan M, et al. (2000) $Na^+$, $K^+$-ATPase isozyme diversity; comparative biochemistry and physiological implications of novel functional interactions. Biosci Rep 20: 51-91.

Non-patent Literature 13: Tsuchiya B, Sato Y, Kameya T, Okayasu I, Mukai K (2006) Differential expression of N-cadherin and E-cadherin in normal human tissues. Arch Histol Cytol. 69: 135-145.

SUMMARY OF INVENTION

Technical Problem

In view of the status quo in the art, an object of the present invention is to provide a molecular marker expressed specifically in corneal endothelial cells, and applied technologies, such as a method for producing corneal endothelial cells using the marker and a method for evaluating corneal endothelial cells using the marker.

Solution to Problem

The present inventors conducted extensive research to achieve the object. The inventors selected, from a database that has an exhaustive coverage of genes expressed in corneal endothelial cells, genes that are highly expressed in corneal endothelial cells, that encode cellular membrane proteins, and that exhibit a low level of expression in other tissues. The inventors examined the expression of the genes in corneal endothelial cells and in other tissues to find genes that specifically express in corneal endothelial cells. They also immunostained human cornea sections to detect proteins encoded by these genes, and confirmed their specific expression in the corneal endothelium. The invention represented by the following subject matter is provided on the basis of these findings.

Item 1.

A method for producing one or more corneal endothelial cells, the method comprising the step of sorting, from a cell population comprising one or more corneal endothelial cells, one or more cells in which at least one member selected from the group consisting of ZP4, MRGPRX3, GRIP1, GLP1R, HTR1D, and CLRN1 is expressed.

Item 2.

The method according to Item 1, wherein the cell population comprising one or more corneal endothelial cells is obtained by inducing differentiation of stem cells.

Item 3.

The method according to Item 1, wherein the cell population comprising one or more corneal endothelial cells is obtained by culturing corneal endothelial cells.

Item 4.

The method according to any one of Items 1 to 3, wherein the sorting step comprises binding one or more antibodies that specifically recognize at least one member selected from the group consisting of ZP4, MRGPRX3, GRIP1, GLP1R, HTR1D, and CLRN1 to the cell population comprising one or more corneal endothelial cells.

Item 5.

A method for evaluating one or more corneal endothelial cells using expression of at least one member selected from the group consisting of ZP4, MRGPRX3, GRIP1, GLP1R, HTR1D, and CLRN1 as an indication.

Item 6.

A marker for detecting one or more corneal endothelial cells, the marker comprising at least one member selected from the group consisting of ZP4, MRGPRX3, GRIP1, GLP1R, HTR1D, and CLRN1.

Item 7.

A kit for detecting one or more corneal endothelial cells, the kit comprising one or more substances that specifically recognize at least one member selected from the group consisting of ZP4, MRGPRX3, GRIP1, GLP1R, HTR1D, and CLRN1.

Advantageous Effects of Invention

A molecular marker that is expressed specifically in corneal endothelial cells is provided, and this marker can specifically detect corneal endothelial cells. The expression product of the molecular marker is a cell-surface protein. Thus, cells are identified and/or sorted in a viable condition. Specifically, the marker can efficiently provide corneal endothelial cells in a viable condition. Because corneal endothelial cells obtained using this marker are suitable for transplantation, the use of the marker not only enables treatment of diseases that require transplant of corneal endothelial cells, but also alleviates the donor shortage in corneal transplantation. The molecular marker is also usable to accurately evaluate cultured corneal endothelial cells for their suitability for transplantation. The present invention is therefore useful in the treatment of various diseases caused by functional disorder of corneal endothelial cells.

DESCRIPTION OF EMBODIMENTS

Figure 1:
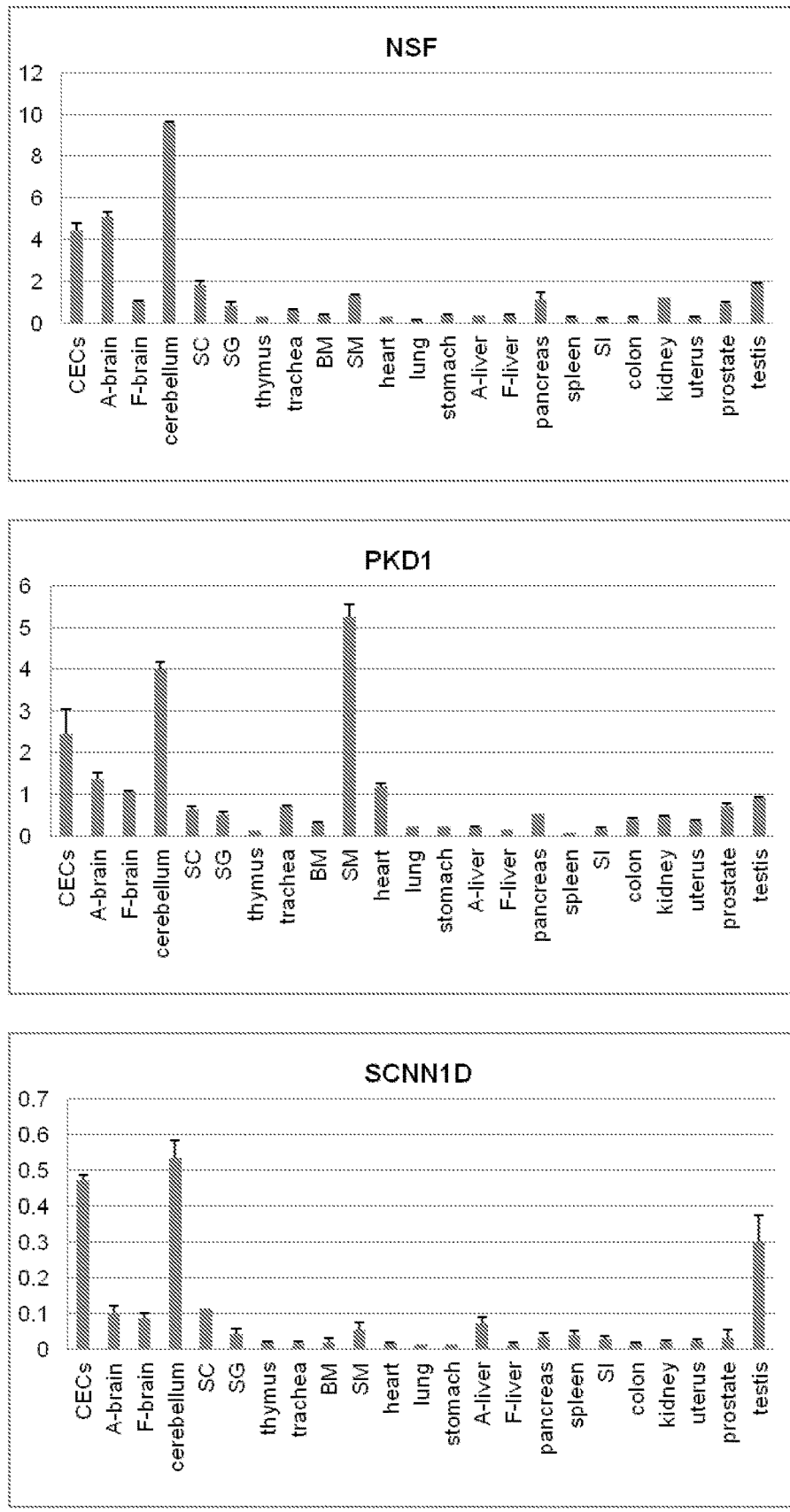
FIG. 1 shows the results of the measurement of expression levels of genes encoding 13 candidate molecules in corneal endothelial cells and in other 22 different tissues. In each chart, abbreviations are used as follows: CECs: corneal endothelial cells, A-brain: adult brain, F-brain: fetal brain, SC: spinal cord, SG: salivary gland, BM: bone marrow, SM: skeletal muscle, A-liver: adult liver, F-liver: fetal liver, SI: small intestine. The vertical axis of each chart indicates a gene expression level relative to the expression level of a control.
Figure 1:
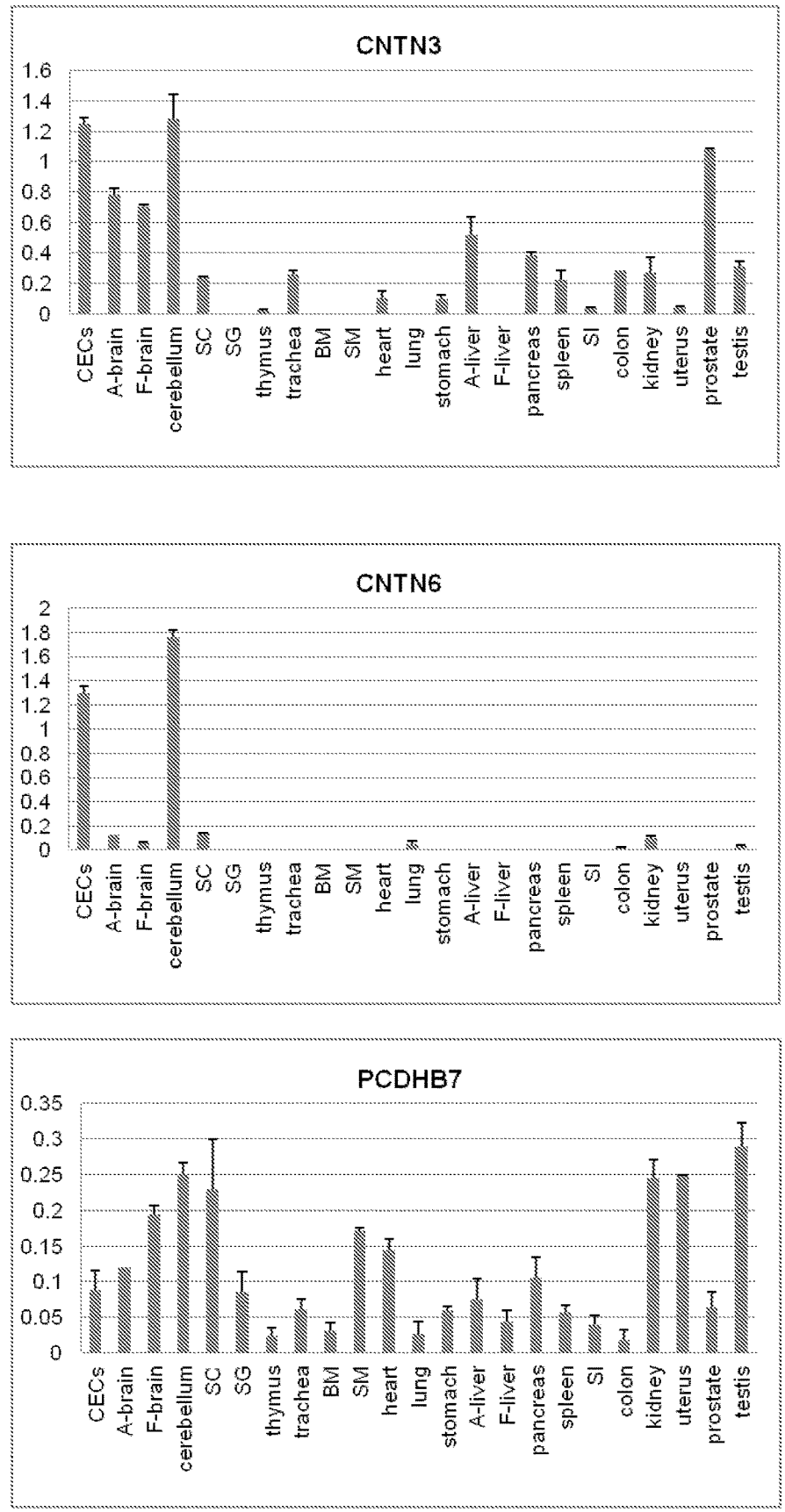
Figure 1:
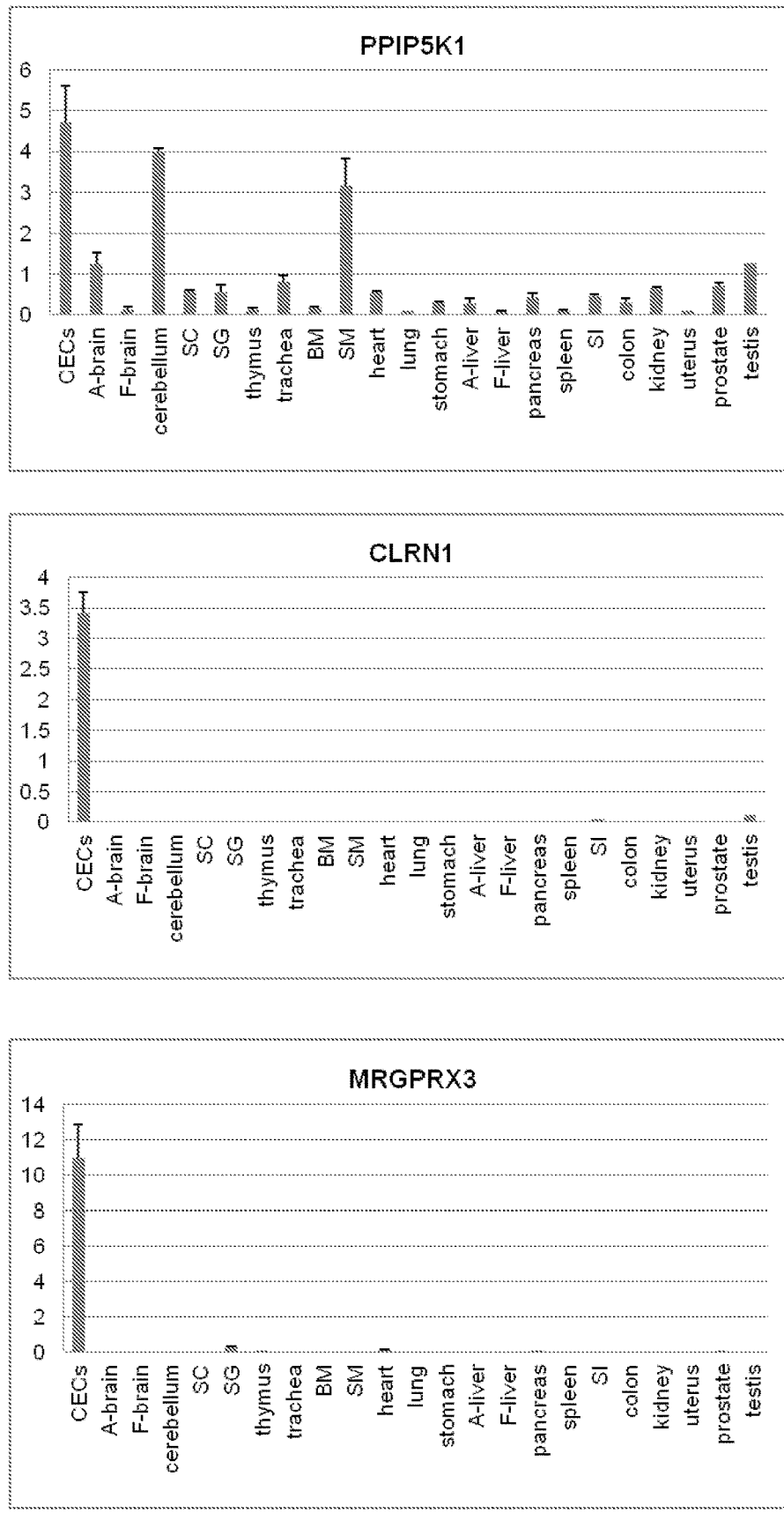
Figure 1:
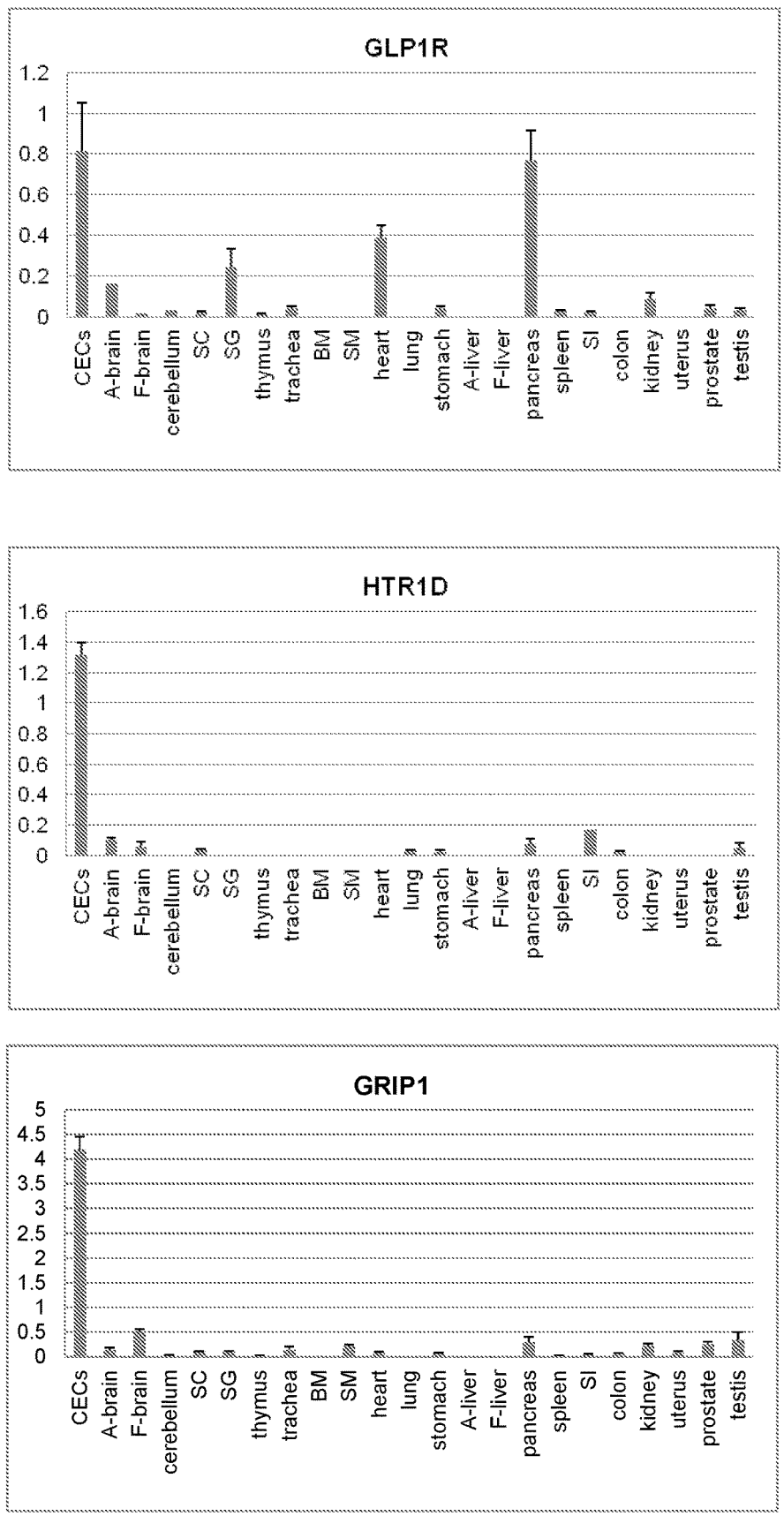
Figure 1:
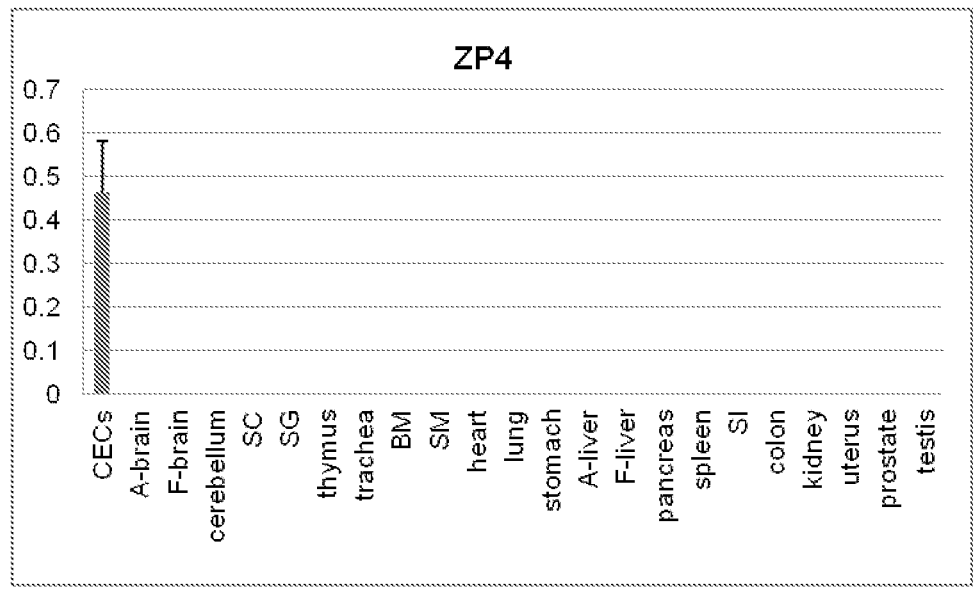

1. Method for Producing Corneal Endothelial Cells 1-1. Cell Population Containing Corneal Endothelial Cells A "cell population containing one or more corneal endothelial cells," which is a starting material for producing one or more corneal endothelial cells, is an assembly of cells including one or more corneal endothelial cells. There is no limitation to the origin and constituents of the cell population, as long as the population contains one or more corneal endothelial cells. For example, the cell population containing one or more corneal endothelial cells encompasses a cell population obtained by artificial differentiation of stem cell(s) and a cell population obtained by culturing corneal endothelial cells isolated from a cornea. Although, in most cases, the cell population containing one or more corneal endothelial cells contains cells other than corneal endothelial cells, the population may contain only one or more corneal endothelial cells. The origin of the cell population containing one or more corneal endothelial cells is not particularly limited, but is preferably a human.

For example, the percentage of corneal endothelial cells present in the cell population containing one or more corneal endothelial cells is 1% or more, 5% or more, 10% or more, 20% or more, 30% or more, 40% or more, 50% or more, 60% or more, 70% or more, or 80% or more, based on the total number of cells.

Stem cells for use in preparing the cell population containing one or more corneal endothelial cells are not particularly limited, as long as the stem cells can be cultured in vitro and can be differentiated into corneal endothelial cells. The stem cells for use may be suitably selected from any stem cells known and hereafter developed in the art. Examples of such stem cells include artificial pluripotent stem cells (induced pluripotent stem cells: iPS cells), embryonic stem cells (ES cells), fetal primordial germ cell-derived pluripotent stem cells (EG cells), testis-derived pluripotent stem cells (GS cells), and human somatic stem cells capable of differentiating into corneal endothelial cells (tissue stem cells).

iPS cells can be obtained by any available technique, for example, by introducing DNA- or protein-form specific reprogramming factors into somatic cells. Examples of reprogramming factors include Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, beta-catenin, Lin28b, Sall1, Sall4, Esrrb, Nr5a2, Tbx3, and Glis1. These reprogramming factors may be used singly or in any combination. Examples of combinations of reprogramming factors are disclosed in, for example, WO2007/069666, WO2008/118820, WO2009/007852, WO2009/032194, WO2009/058413, and WO2009/057831. The type of somatic cells is not particularly limited, and somatic cells for use include any cells that have been confirmed to produce iPS cells and any cells hereafter reported to produce iPS cells. In an embodiment, examples of preferable somatic cells include fibroblasts and white blood cells. The somatic cells are preferably derived from humans.

ES cells are obtained by any available technique. For example, ES cells can be established by removing the inner cell mass from the blastocyst of a fertilized egg from a mammal (preferably, a human), and culturing the inner cell mass on a feeder of fibroblasts. The mammal is not particularly limited, but is preferably a human. ES cells in passage culture can be maintained using a culture solution containing substances, such as a leukemia inhibitory factor (LIF) and/or a basic fibroblast growth factor (bFGF). ES cells can be selected, for example, using expression of gene markers, such as OCT-3/4, NANOG, and ECAD as an indication.

EG cells are pluripotent cells as with ES cells, and are established from primordial germ cells in the fetal stage. EG cells are established by culturing primordial germ cells in the presence of substances, such as LIF, bFGF, and stem cell factors (Y. Matsui et al. (1992), Cell, 70: 841-847; J. L. Resnick et al. (1992), Nature, 359: 550-551).

GS cells are testis-derived pluripotent stem cells, and are the origin of sperm formation. These cells can be induced to differentiate into a variety of cell lineages like ES cells. GS cells can be self-renewed in a culture solution containing a glial cell line-derived neurotrophic factor (GDNF). Repeated passage under the same conditions as those for ES cells produces sperm stem cells (M. Kanatsu-Shinohara et al. (2003) Biol. Reprod., 69: 612-616).

Examples of somatic stem cells that can be differentiated into corneal endothelial cells include neural crest stem cells derived from the corneal stroma (COPs), mesenchymal stem cells, and skin-derived pluripotent precursor cells (skin-derived precursors: SKPs), with COPs and SKPs being preferable. COPs can be prepared, for example, by removing the epithelium and endothelium from a cornea, treating the corneal stroma with a collagenase, and culturing the separated cells in a DMEM/F12 medium containing EGF, FGF2, B27 supplements and LIF. SKPs can be prepared, for example, in accordance with the procedure described in Nat Cell Biol., 2001, vol. 3, 778-784.

In an embodiment, preferable stem cells are iPS cells. In another embodiment, preferable stem cells are neural crest stem cells, and more preferable stem cells are iPS cell-derived neural crest stem cells and corneal stroma-derived neural crest stem cells. The neural crest stem cells, which are pluripotent stem cells that have a self-renewal potential and multilineage potential, are known to migrate out from behind of the neural tube across the body during the development of a vertebrate, and contribute to formation of various tissues. iPS cells can be induced into neural crest stem cells by a known method in the art, or a method according thereto (e.g., the method described in Nature Protocols, 2010, vol. 5, No. 4, 688-701). The use of neural crest stem cells enables efficient differentiation induction into corneal endothelial cells.

The method for inducing differentiation of the stem cells described above into corneal endothelial cells is not particularly limited, and any method known or hereafter developed in the art can be used. For example, the differentiation induction can be performed by the method disclosed in Patent Literature 4. Specifically, stem cells can be differentiated into corneal endothelial cells by culturing the stem cells in a medium that is suitable for culturing stem cells (e.g., MEM medium) and that contains at least one differentiation-inducing factor selected from the group consisting of a GSK3 inhibitor, retinoic acid, TGFb2, insulin, and a ROCK inhibitor at 30 to 40° C. in 1 to 10% $CO_2$ for about several days to one and a half months. The at least one differentiation-inducing factor preferably contains a GSK3 inhibitor and retinoic acid, more preferably a GSK3 inhibitor, retinoic acid, and a ROCK inhibitor, and still more preferably a GSK3 inhibitor, retinoic acid, a ROCK inhibitor, and insulin.

In the manner described above, a cell population that contains one or more corneal endothelial cells can be obtained from stem cells. The obtained cell population containing one or more corneal endothelial cells may be immediately sorted to obtain corneal endothelial cells, or may be sorted after performing repeated passage for a predetermined period to obtain corneal endothelial cells.

There is no particular limitation to the means for obtaining a cell population containing one or more corneal endothelial cells by culturing corneal endothelial cells isolated from a cornea, and any method known or hereafter developed in the art can be suitably selected for use. For example, a cell population containing one or more corneal endothelial cells can be obtained in accordance with the method disclosed in WO2014/104366. Specifically, a Descemet's membrane is removed from a human corneoscleral tissue with human corneal endothelial cells attached to the Descemet's membrane, and shredded, followed by culture in a medium containing about 0.2% of collagenase in 5% $CO_2$ at 37° C. for 1 to 3 hours. A usable medium is a DME medium containing 15% fetal calf serum (FCS) and a 2 ng/mL basic fibroblast growth factor (bFGF). The fibroblasts are then removed by centrifugation wash, followed by tryptic digestion, thereby obtaining a cell population containing pellet-like corneal endothelial cells (primary culture cells).

The thus-obtained cell population containing one or more corneal endothelial cells may be further cultured in a basal medium typically used for animal cell culture, such as D-MEM and MEM. The concentration of glucose added to the medium is preferably 2.0 g/L or less, and more preferably 0.1 to 1.0 g/L. It is also preferable to add to the medium a growth factor such as a hepatocyte growth factor (HGF), epidermal growth factor (EGF), recombinant EGF (rEGF), and/or fibroblast growth factor (FGF). Of these factors, a single factor or a combination of two or more factors may be added to the medium. The concentration of the growth factor(s) in the medium is typically 1 to 100 ng/mL, and preferably 2 to 5 ng/mL. From the standpoint of efficient culture of corneal endothelial cells, it is preferable to add a 5 to 1,000 μg/mL ascorbic acid derivative, such as ascorbic acid 2-phosphate, to the medium.

The culture of corneal endothelial cells can be performed by adherent culture using a culture vessel (e.g., a dish, a Petri dish, a tissue culture dish, a multidish, a microplate, a microwell plate, a multiplate, a multiwell plate, a chamber slide, a Schale, a tube, a tray, and a cell culture bag) coated with a matrix such as matrigel or collagen. The culture temperature is typically 35 to 38° C., and preferably 37° C. The humidity is typically 90 to 100% humidity, and preferably 100% humidity. The $CO_2$ concentration is typically 5 to 15%, and preferably 10%. It is thus preferable to culture the cells in an incubator capable of maintaining the conditions. The time period for culture is not particularly limited, and, for example, cells can be cultured until the stage at which the cells become confluent (steady state) (e.g., 1 to 5 days).

The cells can optionally be further passaged, after becoming confluent. For example, confluent cells are washed with PBS, and then dispersed using trypsin/EDTA, followed by centrifugation. The cells are then seeded onto a culture vessel containing the same medium as described above at a cell density of 500 to 60,000 cell/cm$^2$, and cultured under the conditions described above. Additionally, the cells can be further repeatedly passaged in the same manner after becoming confluent. This procedure provides a cell population containing corneal endothelial cells that are passage cells.

1-2. Sorting Corneal Endothelial Cells Using Molecular Marker as Indication

In a corneal endothelial cell, the following are specifically expressed: ZP4, MRGPRX3, GRIP1, GLP1R, HTR1D, CLRN1, SCNN1D, PKD1, CNTN6, NSF, CNTN3, PPIP5K1, and/or PCDHB7. Thus, it is possible to produce one or more corneal endothelial cells by sorting out one or more corneal endothelial cells from a cell population containing corneal endothelial cells using the expression of at least one molecule selected from these molecules as an indication. In this specification, ZP4, MRGPRX3, GRIP1, GLP1R, HTR1D, CLRN1, SCNN1D, PKD1, CNTN6, NSF, CNTN3, PPIP5K1, and PCDHB7 are also referred to as molecular markers.

ZP4 is a gene that encodes one of the glycoproteins that form the zona pellucida, which is an extracellular matrix surrounding the oocyte (Hartmann J F, et al., (1972), Proc Natl Acad Sci USA, 69: 2767-2769). Although the greatest portion of the protein resides outside the cell, its carboxyl terminus is a cellular transmembrane domain (Gupta S K, et al. (2012), Cell Tissue Res, 349: 665-678).

MRGPRX3 is a gene that encodes one of the Mas-related G-protein-coupled receptors, and is thought to be involved in modulation of pain in sensory neurons (Lembo P M, et al. (2002), Nat Neurosci 5: 201-209).

GRIP1 is a gene that encodes a protein that binds to the carboxyl terminus of the intracellular domain of an AMPA (a-amino-3-hydroxy-5-methyl-4-isoxazole propionate) glutamic acid receptor, and is reported as being expressed in the synapses and brain (Dong H, et al., (1999), J Neurosci, 19: 6930-6941).

GLP1R is a gene that encodes a receptor of glucagon-like peptide-1, which is one of the incretins that stimulate insulin secretion from β cells in the pancreas (Orskov C, (1992), Diabetologia, 35: 701-711). GLP1R is reported as being expressed in the pancreas (Tornehave D, et al., (2008), J Histochem Cytochem, 56: 841-851).

HTR1D is a gene that encodes one of the serotonin receptors, and is expressed in nerve fibers of the craniofacial tissue. HTR1D is thought to be involved in the development of migraine (Harriott A M, et al., (2008), Cephalalgia, 28: 933-944).

CLRN1 is reported as one of the causative genes for Usher syndrome type IIIa, which causes inner ear disorders and retinitis pigmentosa (Kremer H, et al., (2006), Hum Mol Genet 15 Spec No 2: p. 262-270). CLRN1 is expressed in hair cells in the inner ear and glial cells in the retina, supposedly playing a crucial role in the development and differentiation of hair cells in the inner ear (Geller S F, et al., (2009), PLoS Genet 5: e1000607). However, its exact function remains unknown.

SCNN1D is a gene that encodes the δ subunit of the epithelial Na channel (ENaC), and is reported as being expressed in organs, such as brain, heart, respiratory organ, and kidney (Ji H L et al., (2012), Am J Physiol Lung Cell Mol Physiol. 303: 1013-1026).

PKD1 is a gene that encodes polycystin-1, and is reported as being one of the causative genes of autosomal dominant polycystic kidney (Gabow P A, (1993) N Engl J Med. 329: 332-342). PKD1 is highly expressed in the kidney. Polycystin-1 is suggested as being involved in differentiation of renal tubular epithelial cells (Boletta A et al., (2003) Trends Cell Biol. 13: 484-492).

CNTN6 is a gene that encodes contactin 6. Contactin 6, which is a member of the immunoglobulin superfamily, functions as a cell adhesion molecule. Contactin 6 is suggested as being involved in the formation of synaptic connections during nervous system development (http://www.ncbi.nlm.nih.gov/gene/27255).

NSF is a gene that encodes an N-ethylmaleimide-sensitive factor. This protein forms a conjugate together with SNAP (soluble NSF attachment protein) and SNARE (SNAP receptor) to stimulate the fusion of the synaptic vesicle with the cellular membrane (Sollner T et al., (1993) Nature. 362: 318-324).

CNTN3 is a gene that encodes contactin 3. The structure, as with contactin 6, suggests its role in cell adhesion. CNTN3 is reported as being expressed in the frontal lobe, occipital lobe, cerebellum, etc. (http://www.uniprot.org/uniprot/Q9P232).

PPIP5K1 is a gene that encodes an inositol kinase, and is thought to play a critical role in intracellular signal transduction (Gokhale N A et al., (2013) Biochem J. 453: 413-426).

PCDHB7 is a gene that encodes a protocadherin β7. Although its specific function is unknown, PCDHB7 is suggested as playing a critical role in cell-cell adhesion in the nervous system (http://www.ncbi.nlm.nih.gov/gene/56129).

The molecular marker used as an indication for corneal endothelial cells may be only one member selected from the group consisting of ZP4, MRGPRX3, GRIP1, GLP1R, HTR1D, CLRN1, SCNN1D, PKD1, CNTN6, NSF, CNTN3, PPIP5K1, and PCDHB7, or the marker may be any combination of two or more of these molecules. In an embodiment, the molecular marker is preferably ZP4, MRGPRX3, GRIP1, GLP1R, HTR1D, and CLRN1, more preferably ZP4, MRGPRX3, GRIP1, GLP1R, and HTR1D, still more preferably ZP4, MRGPRX3, GRIP1, and GLP1R, still yet more preferably ZP4, MRGPRX3, and GRIP1, still further more preferably ZP4, and MRGPRX3, and particularly preferably ZP4, because their expression products are surface proteins of corneal endothelial cells and they are expressed highly specifically in corneal endothelial cells.

SCNN1D, PKD1, CNTN6, NSF, CNTN3, PPIP5K1, and PCDHB7 are thought to be also expressed in other tissues, such as the brain, spinal cord, skeletal muscle, or liver, as shown in FIG. 1. However, their expression in these tissues can be ignored by adjusting the type of stem cells from which a cell group containing one or more corneal endothelial cells is derived and/or the conditions under which differentiation of stem cells into corneal endothelial cells are performed, or by using a cell group obtained by culturing corneal endothelial cells as a cell group containing one or more corneal endothelial cells. Thus, these molecular markers are also useful in sorting or detecting corneal endothelial cells. Of these molecular markers, SCNN1D, PKD1, CNTN6, NSF, CNTN3, and PPIP5K1 are preferable, SCNN1D, PKD1, CNTN6, NSF, and CNTN3 are more preferable, SCNN1D, PKD1, CNTN6, and NSF are still more preferable, SCNN1D, PKD1, and CNTN6 are still yet more preferable, SCNN1D and PKD1 are still further more preferable, and SCNN1D is particularly preferable.

Sorting of one or more corneal endothelial cells from a cell population containing one or more corneal endothelial cells using, as an indication, the expression of at least one molecular marker selected from the group consisting of ZP4, MRGPRX3, GRIP1, GLP1R, HTR1D, CLRN1, SCNN1D, PKD1, CNTN6, NSF, CNTN3, PPIP5K1, and PCDHB7 can be performed, for example, by sorting cells in which at least one of the molecular markers is expressed, in the case where the cell population contains corneal endothelial cells but does not contain other cells that allow the expression of the at least one molecular marker. When the cell population contains other cells that allow the expression of the at least one molecular marker in addition to corneal endothelial cells, the cells that exhibit significantly higher expression levels than other cells can be sorted to isolate corneal endothelial cells. The molecular marker for use as an indication may be any combination of two or more, three or more, four or more, or five or more of the molecules.

The expression of the molecular marker can be detected by any available method. Examples of typical detection methods include a method comprising measuring the expression of the gene(s) that encode the at least one molecular marker by RT-PCR, and a method comprising detecting the presence of the at least one molecular marker using a substance that specifically binds to the at least one molecular marker. All of the molecular markers listed above are a surface protein of the corneal endothelial cell. Because the molecular marker can be detected with cells remaining viable, the method comprising detecting a molecular marker using a substance that specifically binds to the marker is preferable.

The type of substance that specifically binds to the molecular marker is not particularly limited. Examples of the substance include antibodies and aptamers. The substance is preferably an antibody or its fragment. The antibody may be either a polyclonal antibody or a monoclonal antibody. Examples of the antibody fragment include Fab fragments, F(ab)$_2$ fragments, and ScFv fragments. When expression of two or more types of molecular markers is used to detect corneal endothelial cells, substances that specifically bind to respective markers may be used in combination. In an embodiment, the substances that specifically bind to respective molecular markers are preferably those that cannot be decomposed by a treatment to separate the cell group containing one or more corneal endothelial cells into individual cells (e.g., treatment with a protease).

The antibody for specifically recognizing a molecular marker for use may be a commercially available antibody, or may be prepared by a well-known method. There are well-known methods for preparing antibodies. For example, a polyclonal antibody can be prepared by immunizing a non-human animal with purified molecular markers or their partial peptides, and obtaining serum of the animal in accordance with an ordinary method. A monoclonal antibody can be obtained from a hybridoma prepared by fusing spleen cells from an immunized animal with myeloma cells.

To facilitate the detection of cells bound to a substance that specifically binds to a molecular marker, the substance is preferably labeled with a labeling substance. The labeling substance is not particularly limited. Examples of labeling substances include fluorescent materials, radioactive materials, chemiluminescent materials, enzymes, biotin, and streptavidin. The substance that specifically binds to a molecular marker may be indirectly labeled. For example, a pre-labeled antibody (a secondary antibody) that specifically binds to the substance (e.g., an antibody) may be used.

The method for recognizing cells bound to a substance that specifically binds to a molecular marker to sort the cells is not particularly limited, and any method known and hereafter developed may suitably be selected. For example, the method for recognizing/sorting cells can be selected according to the type of labeling substance for use. Typical methods for recognizing/sorting cells include fluorescence-activated cell sorting (FACS), magnetic-activated cell sorting (MACS), and affinity chromatography. Because of their capability of simultaneously detecting multiple molecular markers, FACS and MACS are preferable, and FACS using a flow cytometer equipped with a cell sorter is more preferable. The mode of FACS is not particularly limited. For example, FACS may be either a droplet-charge mode or a cell-capturing mode. Corneal endothelial cells can be purified in this manner.

As described above, one or more corneal endothelial cells can be obtained by sorting corneal endothelial cells from a cell population containing one or more corneal endothelial cells using a molecular marker as an indication. The one or more corneal endothelial cells include corneal endothelium precursor cells. Following the method described above, it is also possible to obtain a cell population containing corneal endothelial cells at a significantly high concentration. Thus, the method for producing one or more corneal endothelial cells described above can also be used to purify (enrich) corneal endothelial cells. The percentage of purified (concentrated) corneal endothelial cells in a cell population, on a cell count basis, is, for example, 50% or more, 55% or more, 60% or more, 65% or more, 70% or more, 75% or more, 80% or more, 85% or more, 90% or more, 95% or more, or 99% or more. The corneal endothelial cells and corneal endothelium precursor cells (a cell population containing concentrated corneal endothelial cells and/or corneal endothelium precursor cells) obtained by the method described above can be further cultured. The further culture can be performed, for example, in a differentiation-induction medium so that the corneal endothelial cells become more mature. Examples of such a differentiation-induction medium for use include the above-described medium for inducing differentiation of stem cells into corneal endothelial cells. The further culture can be performed under conditions suitable for proliferation of corneal endothelial cells, or maintenance of the viability of the cells.

1-3. Use of Corneal Endothelial Cells

The corneal endothelial cells obtained by using the molecular marker described above as an indication can be used in the treatment of diseases caused by functional disorder of the corneal endothelium. Thus, there can be provided a pharmaceutical composition containing the corneal endothelial cells for treatment of corneal endothelial diseases. This pharmaceutical composition may further contain various components, scaffold materials, carriers, etc., to aid the maintenance and proliferation of the corneal endothelial cells, or to aid application of the composition to the affected area.

Examples of the components to aid the maintenance and/or proliferation of the cells include components used for mediums, such as carbon sources, nitrogen sources, vitamins, minerals, salts, and various cytokines. Examples of the scaffold materials to aid the application of the composition to the affected area include collagen, polylactic acid, hyaluronic acid, cellulose, and derivatives thereof. These components and scaffold materials may be used in a combination of two or more. The pharmaceutical composition may be in the form of an injectable aqueous solution (e.g., physiological saline; physiological buffers, such as PBS; and isotonic solutions containing glucose and/or other adjuvants) to which corneal endothelial cells have been added. In one embodiment, the pharmaceutical composition containing the corneal endothelial cells is preferably in the form of a suspension in which corneal endothelial cells are homogeneously suspended. In clinical applications, such a suspension has been injected into an eye. The concentration of corneal endothelial cells in the suspension is not particularly limited, and is, for example, $1\times10^4$/ml to $1\times10^8$/ml, or $1\times10^5$/ml to $1\times10^7$/ml.

A corneal endothelial cell sheet can be obtained by culturing corneal endothelial cells obtained using the molecular marker as an indication on a suitable carrier (e.g., a polymer membrane). The carrier is not particularly limited, and examples of the carrier include biopolymers, such as collagen, atelocollagen, alkali-treated collagen, gelatin, keratin, hyaluronic acid, glycosaminoglycan (chondroitin sulfate, dermatan sulfate, hyaluronic acid, heparan sulfate, heparin, keratan sulfate), proteoglycan, alginic acid, chitosan, polyamino acid (polylactic acid), and cellulose; and temperature-responsive polymers, such as (meth)acrylamide compounds, N-(or N,N-di)alkyl substituted (meth)acrylamide derivatives, vinyl ether derivatives, and copolymers thereof. In addition to the sheet form, the corneal endothelial cells may be used in the form of pellets obtained by concentrating the cells, for example, by filter filtration (a mass of cells).

A protectant or similar component may optionally be added to the corneal endothelial cells to cryopreserve the cells. Examples of the protectant include glycerol, DMSO (dimethyl sulfoxide), propylene glycol, and acetamide. To maintain the safety of the cells as a graft, the cells can be subjected to heat treatment and/or radiation treatment, or the like.

There is no particular limitation to the diseases targeted by the treatment using corneal endothelial cells, a pharmaceutical composition containing the cells, or a corneal endothelial cell sheet. Examples of the diseases include corneal endothelial dysfunction including bullous keratopathy, corneal dystrophy, developmental glaucoma, Rieger's anomaly, congenital hereditary endothelial dystrophy, limbal dermoid, sclerocornea, corneal shape irregularities, such as keratoconus and pellucid marginal corneal degeneration, corneal scarring, corneal infiltration, corneal deposits, corneal edema, corneal ulcer, ocular injuries caused by a chemical substance or heat, ocular diseases such as keratitis, corneal degeneration, corneal infection, neuroblastoma, Hirschsprung's disease, Waardenburg syndrome, partial albinism, and von Recklinghausen's disease.

A patient in need of transplant of corneal endothelial cells (e.g., a patient with any of the diseases as described above) can be transplanted with corneal endothelial cells or a corneal endothelial cell sheet to treat their disease. Thus, a method can be provided for treating the diseases listed above, and the method comprises administering the corneal endothelial cells obtained in the method described above to a patient in need of transplant of corneal endothelial cells.

2. Method for Evaluating Corneal Endothelial Cells

The at least one member selected from the group consisting of ZP4, MRGPRX3, GRIP1, GLP1R, HTR1D, CLRN1, SCNN1D, PKD1, CNTN6, NSF, CNTN3, PPIP5K1, and PCDHB7 described above is specifically expressed in corneal endothelial cells. Thus, there can be provided a method for evaluating corneal endothelial cells using expression of the at least one molecular marker as an indication. For example, the at least one molecular marker is measured for their expression level in test cells considered (or presumed) to be corneal endothelial cells. When specific expression (or significant expression) is confirmed, the test cells are determined to be corneal endothelial cells. Preferable molecular markers for use in this evaluation method are the same as those described in section 1-2 above.

There is no particular limitation to the test cells. Examples of test cells include cells obtained by culturing the cells described in section 1-1 above in a medium under conditions suitable for differentiation induction into corneal endothelial cells, and cells obtained by culturing corneal endothelial cells collected from a cornea. The method for measuring the expression level of a molecular marker is not particularly limited. Examples of the method include the measurement method using RT-PCR and the measurement method using a substance that specifically binds to a molecular marker described in section 1-2. Test cells evaluated in this manner can be safely used as corneal endothelial cells.

3. Corneal Endothelial Cell Detection Kit

The invention provides a kit for detecting corneal endothelial cells, and the kit includes a substance that specifically recognizes at least one molecular marker selected from the group consisting of ZP4, MRGPRX3, GRIP1, GLP1R, HTR1D, CLRN1, SCNN1D, PKD1, CNTN6, NSF, CNTN3, PPIP5K1, and PCDHB7. The substance that specifically recognizes at least one molecular marker is not particularly limited. Examples of the substance include the antibodies and aptamers described in section 1-2 above. The kit may include, in addition to the substance that specifically recognizes a molecular marker, any substance used in detection of corneal endothelial cells, a container, a manual guide, etc. For example, the kit may include a labeling substance that labels the substance that specifically recognizes a molecular marker described above.

Examples

The following Examples describe the present invention in more detail. However, the invention is not limited to the Examples.

1. Identification of Candidate Molecules

RNA-seq data (GSE41616, Chen, et al., (2013), Hum Mol Genet 22: 1271-1279) reported by Chen et al. were obtained from a gene expression information database (Gene Expression Omnibus: GEO) to use as information of genes expressed in corneal endothelial cells in humans in vivo. The data include information of RNAs expressed in corneal endothelial cells obtained from three adult donors (31, 56, and 64 years old), and information of RNAs expressed in corneal endothelial cells obtained from two fetal donors (16 to 18 weeks). To confirm the data integrity, the information of corneal epithelial cell specific markers KRT3 and KRT12 were examined, and high expression levels of KRT3 and KRT12 in the 56-year-old adult donor-derived corneal endothelial cells was confirmed. Because the sample derived from this donor was likely contaminated with corneal epithelial cells, data of the remaining four donors were used for the following analysis.

RNA-seq reads were aligned to the human reference genome (hg19) by using TopHat (version 1.4.1), and the results were used to assemble transcript models by Cufflinks package (version 2.1.1) (Trapnell, et al., (2012), Nat. Protoc. 7: 562-578). The gene expression levels were quantified as FPKM (Fragments Per Kilobase of exon per Million mapped fragments: FPKM) using Cufflinks, and genes expressed in corneal endothelial cells at 10 FPKM or more were selected; more specifically, 10,627 genes were selected. Subsequently, these genes were narrowed down to only genes encoding cellular membrane proteins using GO terms listed in Table 1. As a result, the genes were narrowed down to 1494 genes, as shown in Table 1. Of these, 1075 genes were expressed in both adult and fetal corneal endothelial cells, 225 genes were expressed in only adult corneal endothelial cells, and 194 genes were expressed in only fetal corneal endothelial cells.

TABLE 1

| GO Term | GO ID | Both | Adult | Fetal |
|---|---|---|---|---|
| Plasma Membrane | GO: 0005886 | 762 | 155 | 124 |
| Integral to Plasma Membrane | GO: 0005887 | 215 | 49 | 57 |

TABLE 1-continued

| GO Term | GO ID | Both | Adult | Fetal |
|---|---|---|---|---|
| Cell Surface | GO: 0009986 | 111 | 20 | 28 |
| Apical Plasma Membrane | GO: 0016324 | 59 | 18 | 9 |
| Basolateral Plasma Membrane | GO: 0016323 | 50 | 12 | 8 |
| External Side of Plasma Membrane | GO: 0009897 | 31 | 9 | 9 |
| Lateral Plasma Membrane | GO: 0016328 | 10 | 0 | 4 |
| Basal Plasma Membrane | GO: 0009925 | 8 | 2 | 2 |
| Extrinsic to Plasma Membrane | GO: 0019897 | 8 | 2 | 0 |
| Apicolateral Plasma Membrane | GO: 0016327 | 5 | 0 | 1 |
| Anchored to External Side of Plasma Membrane | GO: 0031362 | 4 | 0 | 0 |
| Anchored to Plasma Membrane | GO: 0046658 | 2 | 2 | 0 |
| Extrinsic to External Side of Plasma Membrane | GO: 0031232 | 2 | 0 | 0 |
| Intrinsic to External Side of Plasma Membrane | GO: 0031233 | 1 | 1 | 0 |
| Intrinsic to Plasma Membrane | GO: 0031226 | 1 | 1 | 0 |
| Cell Outer Membrane | GO: 0009279 | 1 | 0 | 0 |
| External Side of Cell Outer Membrane | GO: 0031240 | 0 | 0 | 0 |
| Integral to Cell Outer Membrane | GO: 0045203 | 0 | 0 | 0 |
| Total | | 1,075 | 225 | 194 |

Finally, genes that expressed at 10 TPM or more (tags per million) in 5 or more tissues or cell species were discarded on the basis of the FANTOM5 (Functional Annotation of the Mammalian Genome 5) database. This narrowed down genes encoding candidate molecules to the 13 genes shown in Table 2 below.

TABLE 2

| | RNA-seq FPKM Value | | FANTOM5 CAGE | |
|---|---|---|---|---|
| Gene | Adult CEC | Fetal CEC | Primary Sample Expresses Highest (tpm) | Primary Samples Express >10 tpm |
| Genes Highly expressed in only adult CECs | | | | |
| PPIP5K1 | 17.39 | 6.17 | none | 0 |
| CLRN1 | 14.15 | 0.56 | lens epithelial cells (22.91) | 2 |
| MRGPRX3 | 11.16 | 0.26 | Malassez-derived cells (26.14) | 1 |
| GLP1R | 10.85 | 2.64 | fetal heart (10.51) | 1 |
| Genes Highly expressed in only fetal CECs | | | | |
| CNTN3 | 5.36 | 19.86 | none | 0 |
| PCDHB7 | 1.11 | 11.14 | dura mater (9.37) | 0 |
| HTR1D | 7.41 | 10.48 | small intestine (12) | 2 |
| Genes Highly expressed in both adult and fetal CECs | | | | |
| GRIP1 | 39.33 | 22.70 | fetal temporal lobe (6.46) | 0 |
| NSF | 31.58 | 14.09 | pineal gland (7.84) | 0 |
| PKD1 | 24.99 | 38.47 | aorta (8.45) | 0 |
| SCNN1D | 21.72 | 28.05 | granulocyte macrophage progenitor (22.21) | 4 |
| ZP4 | 12.22 | 56.52 | none | 0 |
| CNTN6 | 11.48 | 22.09 | cerebellum (24.20) | 4 |

2. RNA Expression Levels of Candidate Molecules in Ocular Tissues and Whole Body Tissues To confirm the expression levels of the 13 genes narrowed down in section 1 above in corneal endothelial cells and the whole body tissues, quantitative PCR was performed to examine their RNA expression levels in adult human corneal endothelial cells and 22 other tissues. The details of the procedure will be described later. The results reveal that all of the genes were expressed in corneal endothelial cells, which is consistent with the results of the data analysis as shown in FIG. 1. In particular, ZP4, MRGPRX3, GRIP1, GLP1R, HTR1D, and CLRN1 exhibited the highest expression levels in corneal endothelial cells than in other tissues, while their expression was also confirmed in only a few other tissues.

Figure 2:
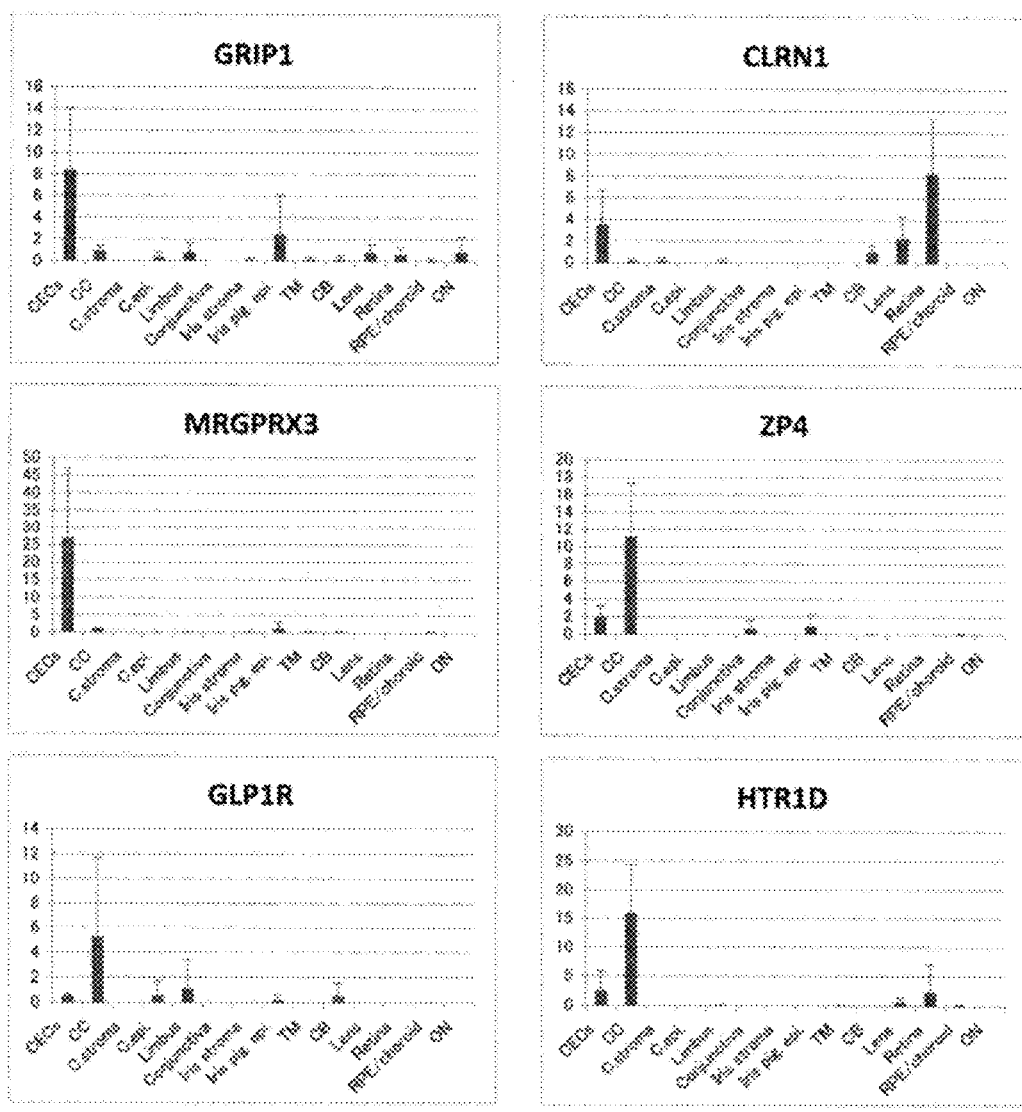
FIG. 2 shows the results of the measurement of expression levels of genes encoding candidate molecules in ocular tissues. The measurement was performed by quantitative PCR. In each chart, abbreviations are used as follows: CECs: corneal endothelial cells, CC: cultured corneal endothelial cells, C. stroma: corneal stroma, C. epi: corneal epithelium, Limbus: corneal limbus, Iris pig. epi: iris pigment epithelial cells, TM: trabecular meshwork, CB: ciliary body, RPE/choroid: retinal pigment epithelium/choroid, and ON: optic nerve. The vertical axis of each chart indicates a gene expression level relative to the expression level of a control.

Subsequently, quantitative PCR was performed on these 6 genes to confirm their expression levels across ocular tissues. To prepare ocular tissues, four eyeballs from two adult donors were used. As shown in FIG. 2, all of the genes were confirmed to exhibit high expression levels in corneal endothelial cells. Given that the corneal stroma is adjacent to the corneal endothelium and originates from the cranial neural crest as with corneal endothelial cells, the absence of expression or lower expression levels in the corneal stroma is considered to be one of the important features for a corneal endothelial cell marker. CLRN1 was expressed at a substantially low level in the corneal stroma, and the other 5 genes were not expressed in the corneal stroma. The results indicate that all of these molecules are useful as markers specific to corneal endothelial cells.

Extraction of RNA from corneal endothelial cells was performed in accordance with the following procedure. All human samples were handled according to the tenets of the Declaration of Helsinki. Research-grade corneoscleral rim and whole eyeballs from a human donor were procured from Sight Life (Seattle, Wash.). The corneoscleral tissues were immersed and preserved in Optisol-GS (Bausch & Lomb, Rochester, N.Y.) at 4° C., and used within 4 days from the death of the donor. The age of the donor was 58 years old. The corneoscleral rim was washed with phosphate-buffered saline (PBS) three times, and the corneal endothelium and Descemet's membrane were dissected along Schwalbe's line with tweezers. From the dissected corneal endothelium, RNA was extracted with a Qiagen miRNeasy Mini Kit (QIAGEN Inc.).

Extraction of RNA from cultured corneal endothelial cells was performed in accordance with the following procedure. Corneoscleral rims were obtained from 4 eyeballs from 4 donors. The ages of the donors ranged from 14 to 25 years. The corneal endothelia and Descemet's membranes were isolated as described above. The isolated tissues were incubated in a Dulbecco's modified Eagle medium (DMEM; Invitrogen) containing 1.2 U/mL dispase II (Godo Shusei Co., Ltd.) and 1% Antibiotic-Antimycotic (Anti-Anti; Invitrogen/Gibco) at 37° C. for 1 hour to isolate the corneal endothelial cells from the Descemet's membranes. The isolated corneal endothelial cells were gently centrifuged and colleted, and then suspended in a DMEM medium containing 50 U/mL penicillin, 50 μg/mL streptomycin, 10% fetal bovine serum (ICN Biomedicals, Inc., Aurora, Ohio), and 2 ng/mL basic fibroblast growth factor (bFGF; Invitrogen). The cells were seeded on dishes coated with a cell attachment reagent (FNC coating mix; Athena ES, Baltimore, Md.), and incubated at 37° C. in a humidified atmosphere of 5% $CO_2$. RNA was then extracted using an Isogen RNA extraction kit. All the cells used for RNA extraction were those harvested during the first passage.

Extraction of RNA from human ocular tissues was performed in accordance with the following procedure. Four eyeballs from 2 donors were preserved in a moist chamber at 4° C., and were used within 5 days from the death of the donors. The ages of the donors were 75 and 79 years old. First, corneoscleral tissues were prepared, and the ciliary body, iris, and lens were isolated from the anterior segment of each eye, and then the iris stroma and iris pigment epithelial cells were isolated. The corneal endothelium and Descemet's membrane were peeled in the manner described above, and the trabecular meshwork was isolated. Further, the conjunctiva was dissected from the corneoscleral tissue, and the central cornea part and limbal part separated with an 8.0-mm diameter trephine were treated with Dispase I (Godo Shusei Co., Ltd., Tokyo) at 4° C. overnight. The corneal epithelium and limbal epithelium were separated from the stroma. The neural retina was peeled from the posterior segment of each eye with tweezers, and the retina pigment epithelial cells (RPE) and choroid were removed together as a cluster. Finally, the optic nerve was isolated. RNAs of all these isolated tissues were extracted using an ISOGEN RNA extraction kit.

For RNA samples from the whole human body tissues except for ocular tissues, Human Total RNA Master Panel II (#636643; Clontech, Mountain View, Calif.) was purchased. Because this product did not include kidney RNA and pancreas RNA, Human Kidney Total RNA (#AM7976; Ambion, Austin, Tex.) and Human Pancreas Total RNA (#AM7954; Ambion) were also separately purchased.

Reverse transcription quantitative polymerase chain reaction (RT-qPCR) was performed in accordance with the following procedure. cDNA was reverse-transcribed from each RNA with a SuperScript III First-Strand Synthesis System (Invitrogen, Carlsbad, Calif.), and quantitative real-time PCR (an initial cycle at 95° C. for 30 sec, followed by 45 cycles of 95° C. for 5 sec, 60° C. for 30 sec, and 72° C. for 30 sec) was performed to quantify cDNA. SYBR Premix Dimer Eraser (Takara Bio Inc., Shiga, Japan) was used, and the internal control used was β-actin (ACTB). Table 3 shows the list of primers used.

TABLE 3

| Gene | Forward/Reverse | Primer Base Sequence | SEQ No. | Accession Number |
|---|---|---|---|---|
| ACTB | Forward | 5'-ACAGAGCCTCGCCTTTGC-3' | SEQ NO. 1 | NM_001101 |
|  | Reverse | 5'-GCGGCGATATCATCATCC-3' | SEQ NO. 2 |  |
| GRIP1 | Forward | 5'-ATGTGGACAAGAAGCAGCAC-3' | SEQ NO. 3 | NM_021150 |
|  | Reverse | 5'-GGAGTTTTGGCAACTTCGAC-3' | SEQ NO. 4 |  |
| NSF | Forward | 5'-CCTATTGGCCCTCGATTTTC-3' | SEQ NO. 5 | NM_006178 |
|  | Reverse | 5'-GGCTAGTGGTCCCAATGATAAG-3' | SEQ NO. 6 |  |
| PKD1 | Forward | 5'-AAGACACCCACATGGAAACG-3' | SEQ NO. 7 | NM_001009944 |
|  | Reverse | 5'-CCAGCGTCTCTGTCTTCTCC-3' | SEQ NO. 8 |  |
| SCNN1D | Forward | 5'-TGGAGCTGCTACACAACACC-3' | SEQ NO. 9 | NM_001130413 |
|  | Reverse | 5'-GAGCAGGTCTCCACCATCAG-3' | SEQ NO. 10 |  |

TABLE 3-continued

| Gene | Forward/Reverse | Primer Base Sequence | SEQ No. | Accession Number |
|---|---|---|---|---|
| ZP4 | Forward | 5'-AAACAGGCCCTCAGGGGA-3' | SEQ NO. 11 | NM_021186 |
| | Reverse | 5'-GACAGGTCACCACACAGGAT-3' | SEQ NO. 12 | |
| CNTN6 | Forward | 5'-TTCTGAGTCGGAAGGCAAAG-3' | SEQ NO. 13 | NM_014461 |
| | Reverse | 5'-CGGACAGATACTGTGCTTCTTG-3' | SEQ NO. 14 | |
| PPIP5K1 | Forward | 5'-CTTTCCCTACGTCAAGTGAGTG-3' | SEQ NO. 15 | NM_014659 |
| | Reverse | 5'-GCTGCTGTGCATGGAATC-3' | SEQ NO. 16 | |
| CLRN1 | Forward | 5'-AATGCAGTACGGGCTTTTCC-3' | SEQ NO. 17 | NM_174878 |
| | Reverse | 5'-GCTCACTGGGATTGCTTTG-3' | SEQ NO. 18 | |
| MRGPRX3 | Forward | 5'-GGAGGTCTTCACCACTGGAC-3' | SEQ NO. 19 | NM_054031 |
| | Reverse | 5'-ACCCAAGACTGGGATGGTTG-3' | SEQ NO. 20 | |
| GLP1R | Forward | 5'-GCAGAAATGGCGAGAATACC-3' | SEQ NO. 21 | NM_002062 |
| | Reverse | 5'-TTCATCGAAGGTCGGTTG-3' | SEQ NO. 22 | |
| CNTN3 | Forward | 5'-CCATGGAAACAGTTGATCCTG-3' | SEQ NO. 23 | NM_020872 |
| | Reverse | 5'-GCTGTTGCTGGGTTCTTTG-3' | SEQ NO. 24 | |
| PCDHB7 | Forward | 5'-GATTTTGTGCGGTCGCTCTAC-3' | SEQ NO. 25 | NM_013940 |
| | Reverse | 5'-TCCCCATTACTTCCGGTATC-3' | SEQ NO. 26 | |
| HTR1D | Forward | 5'-CATGCGTTTCTTCCACTGAG-3' | SEQ NO. 27 | NM_000864 |
| | Reverse | 5'-CATCGGCACTGCAAATACTG-3' | SEQ NO. 28 | |

3. Immunostaining of Corneal Endothelial Cells in Corneal Tissue

Figure 3:
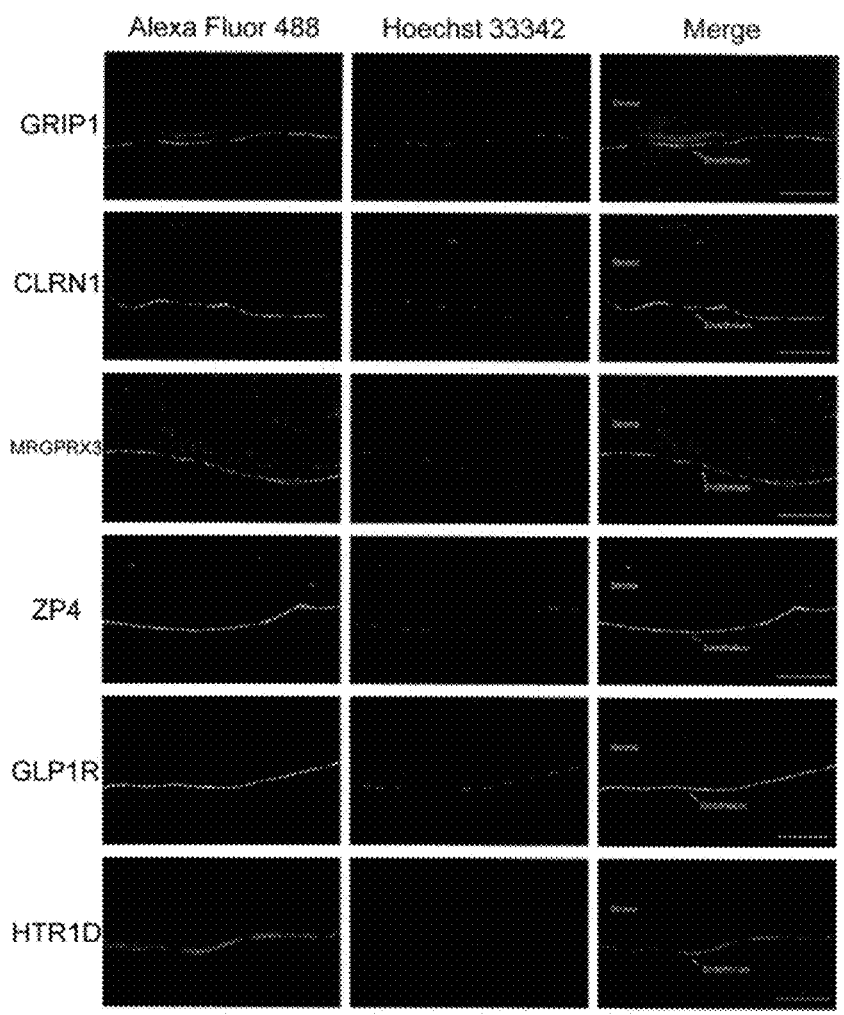
FIG. 3 shows the results of immunostaining of human corneal sections to detect 6 proteins (GRIP1, CLRN1, MRGPRX3, ZP4, GLP1R, and HTR1D).

To confirm the expression of the 6 genes in protein level, corneal tissue sections from a human donor were immunostained using the antibodies shown in Table 4 below. As shown in FIG. 3, in every protein staining, the corneal endothelium was intensely stained. In particular, the three antibodies anti-ZP4 antibody, anti-GLP antibody, and anti-HTR1D antibody specifically stained only the corneal endothelium. Although the corneal stroma was also stained by GRIP1, CLRN1, and MRGPRX3, the fluorescence intensity was clearly lower than the intensity in the corneal endothelial cells. It is thus possible to discriminate corneal endothelial cells from a corneal stroma on the basis of this significant difference in expression level. As noted above, the 6 genes and proteins encoded by the 6 genes were found to be useful as markers to specifically recognize corneal endothelial cells.

The immunostaining was performed in accordance with the following procedure. Corneoscleral tissues were used within 11 days after the death of the donor. The age of the donor was 27 years old. The corneoscleral rim was embedded in optimal cutting temperature (OCT) compound, and frozen sections were cut using a microtome-cryostat (HM560, Thermo Fisher Scientific Inc., Walldorf, Germany) into pieces of 10 µm. After drying at room temperature for 30 minutes, the tissue sections were washed with Tris-buffered saline (TBS; Takara Bio Inc.) 3 times, and incubated with TBS containing 5% donkey serum and 0.3% Triton X-100 for 1 hour to block non-specific reactions. The sections were then incubated with respective primary antibodies listed in Table 4 at 4° C. overnight. Subsequently, the sections were again washed with TBS 3 times, and incubated with a 1:200 dilution of their respective Alexa Fluor 488-conjugated secondary antibodies (Life Technologies) and a 1:100 dilution of Hoechst 33342 (#B2261, Sigma-Aldrich)

TABLE 4

| Antibody | Source | Species and Type | Dilution Used |
|---|---|---|---|
| GRIP1 glutamate receptor interacting protein 1 Cat No. ab122514 | Abcam, Cambridge, MA | Rabbit Polyclonal Antibody | 1:100 |
| ZP4 zona pellucida glycoprotein 4 Cat No. LS-C160968 | LifeSpan BioSciences, Inc. Seattle, WA | Rabbit Polyclonal Antibody | 1:50 |
| CLRN1 clarin 1 Cat. No. sc-69073 | Santa Cruz Biotechnology, Inc. Santa Cruz, CA | Goat Polyclonal Antibody | 1:50 |
| MRGPRX3 MAS-related GPR, member X3 Cat No. ab140863 | Abcam, Cambridge, MA | Rabbit Polyclonal Antibody | 1:25 |
| GLP1R glucagon-like peptide 1 receptor Cat No. GTX44806 | Genetex Inc., Irvine, CA | Rabbit Polyclonal Antibody | 1:100 |
| HTR1D 5-hydroxytryptamine receptor 1D Cat No. ab140486 | Abcam, Cambridge, MA | Rabbit Polyclonal Antibody | 1:150 | at room temperature for 2 hours. The sections were observed with a fluorescent microscope (Axio Observer Dl; Carl Zeiss Jena GmbH, Jena, Germany).

4. Expression of ZP4 in Corneal Endothelial Cells Induced from Human iPS Cells

Figure 4:
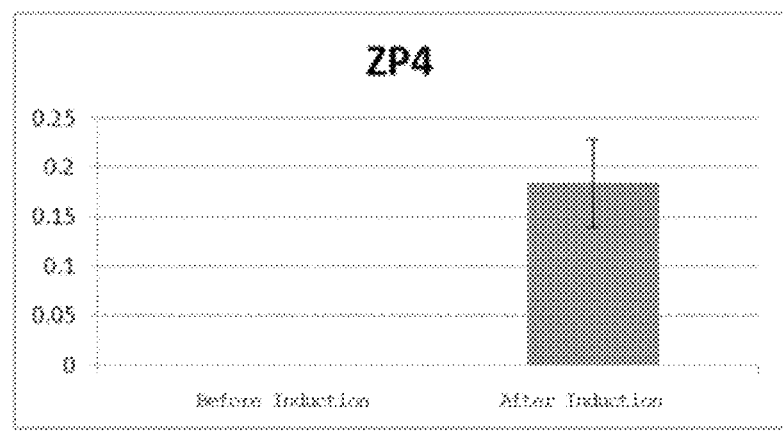
FIG. 4 shows expression levels of ZP4 before and after the induction of human iPS cells into corneal endothelial cells.

Corneal endothelial cells were induced from human iPS cells (provided from the Center for iPS Cell Research and Application, Kyoto University), which are pluripotent stem cells. As shown in FIG. 4, the expression level of ZP4 was increased by induction. The expression of ZP4 was measured with RT-PCR. The expression of ZP4 specific to corneal endothelial cells and the precursor cells indicates that ZP4 is a useful marker to produce corneal endothelial cells and evaluate corneal endothelial cells.

SEQUENCE TABLE

PCT_corneal endothelial cell marker_20150903_144718_4.txt

The invention claimed is:

1. A method for producing a corneal endothelial cell, the method comprising:
   (a) inducing corneal endothelial cell differentiation in a population of stem cells, and
   (b) screening differentiated cells in (a) for expression of at least one cell marker selected from the group consisting of Zona pellucida sperm-binding protein 4 (ZP4), Mas-related G-protein coupled receptor member X3 (MRGPRX3), glucagon-like peptide-1 receptor (GLP1R), 5-hydroxytryptamine receptor 1D (HTR1D), and Clarin-1 (CLRN1), wherein a differentiated cell expressing at least one of the cell markers is a corneal endothelial cell.

2. The method according to claim 1, wherein the screening comprises adding to the differentiated cells of (a) an antibody that specifically recognizes at least one of the cell markers, under conditions permitting binding of the antibody to one of the markers.

3. A method for identifying a corneal endothelial cell in a population of cells obtained by inducing differentiation of stem cells into corneal endothelial cells, the method comprising identifying a cell expressing at least two cell markers selected from the group consisting of ZP4, MRGPRX3, Glutamate receptor-interacting protein 1 (GRIP1), GLP1R, HTR1D, and CLRN1 in a population of cells.

4. The method according to claim 1, wherein the corneal endothelial cell expresses at least two of the markers.

5. The method according to claim 1, wherein the corneal endothelial cell expresses at least three of the markers.

* * * * *

SEQUENCE LISTING

<160> NUMBER OF SEQ ID NOS: 28

<210> SEQ ID NO 1
<211> LENGTH: 18
<212> TYPE: DNA
<213> ORGANISM: Homo sapiens

<400> SEQUENCE: 1
acagagcctc gcctttgc                                                 18

<210> SEQ ID NO 2
<211> LENGTH: 18
<212> TYPE: DNA
<213> ORGANISM: Homo sapiens

<400> SEQUENCE: 2
gcggcgatat catcatcc                                                 18

<210> SEQ ID NO 3
<211> LENGTH: 20
<212> TYPE: DNA
<213> ORGANISM: Homo sapiens

<400> SEQUENCE: 3
atgtggacaa gaagcagcac                                               20

<210> SEQ ID NO 4
<211> LENGTH: 20
<212> TYPE: DNA
<213> ORGANISM: Homo sapiens

<400> SEQUENCE: 4
ggagttttgg caacttcgac                                               20

<210> SEQ ID NO 5
<211> LENGTH: 20
<212> TYPE: DNA
<213> ORGANISM: Homo sapiens

<400> SEQUENCE: 5
cctattggcc ctcgattttc                                               20

<210> SEQ ID NO 6
<211> LENGTH: 22
<212> TYPE: DNA
<213> ORGANISM: Homo sapiens

<400> SEQUENCE: 6
ggctagtggt cccaatgata ag                                            22

<210> SEQ ID NO 7
<211> LENGTH: 20
<212> TYPE: DNA

```
<213> ORGANISM: Homo sapiens

<400> SEQUENCE: 7
aagacaccca catggaaacg                                               20

<210> SEQ ID NO 8
<211> LENGTH: 20
<212> TYPE: DNA
<213> ORGANISM: Homo sapiens

<400> SEQUENCE: 8
ccagcgtctc tgtcttctcc                                               20

<210> SEQ ID NO 9
<211> LENGTH: 20
<212> TYPE: DNA
<213> ORGANISM: Homo sapiens

<400> SEQUENCE: 9
tggagctgct acacaacacc                                               20

<210> SEQ ID NO 10
<211> LENGTH: 20
<212> TYPE: DNA
<213> ORGANISM: Homo sapiens

<400> SEQUENCE: 10
gagcaggtct ccaccatcag                                               20

<210> SEQ ID NO 11
<211> LENGTH: 18
<212> TYPE: DNA
<213> ORGANISM: Homo sapiens

<400> SEQUENCE: 11
aaacaggccc tcagggga                                                 18

<210> SEQ ID NO 12
<211> LENGTH: 20
<212> TYPE: DNA
<213> ORGANISM: Homo sapiens

<400> SEQUENCE: 12
gacaggtcac cacacaggat                                               20

<210> SEQ ID NO 13
<211> LENGTH: 20
<212> TYPE: DNA
<213> ORGANISM: Homo sapiens

<400> SEQUENCE: 13
ttctgagtcg gaaggcaaag                                               20

<210> SEQ ID NO 14
<211> LENGTH: 22
<212> TYPE: DNA
<213> ORGANISM: Homo sapiens

<400> SEQUENCE: 14
cggacagata ctgtgcttct tg                                            22

<210> SEQ ID NO 15
<211> LENGTH: 22
```

```
<212> TYPE: DNA
<213> ORGANISM: Homo sapiens

<400> SEQUENCE: 15
ctttccctac gtcaagtgag tg                                           22

<210> SEQ ID NO 16
<211> LENGTH: 18
<212> TYPE: DNA
<213> ORGANISM: Homo sapiens

<400> SEQUENCE: 16
gctgctgtgc atggaatc                                                18

<210> SEQ ID NO 17
<211> LENGTH: 20
<212> TYPE: DNA
<213> ORGANISM: Homo sapiens

<400> SEQUENCE: 17
aatgcagtac gggcttttcc                                              20

<210> SEQ ID NO 18
<211> LENGTH: 19
<212> TYPE: DNA
<213> ORGANISM: Homo sapiens

<400> SEQUENCE: 18
gctcactggg attgctttg                                               19

<210> SEQ ID NO 19
<211> LENGTH: 20
<212> TYPE: DNA
<213> ORGANISM: Homo sapiens

<400> SEQUENCE: 19
ggaggtcttc accactggac                                              20

<210> SEQ ID NO 20
<211> LENGTH: 20
<212> TYPE: DNA
<213> ORGANISM: Homo sapiens

<400> SEQUENCE: 20
acccaagact gggatggttg                                              20

<210> SEQ ID NO 21
<211> LENGTH: 20
<212> TYPE: DNA
<213> ORGANISM: Homo sapiens

<400> SEQUENCE: 21
gcagaaatgg cgagaatacc                                              20

<210> SEQ ID NO 22
<211> LENGTH: 19
<212> TYPE: DNA
<213> ORGANISM: Homo sapiens

<400> SEQUENCE: 22
ttcatcgaag gtccggttg                                               19

<210> SEQ ID NO 23
```

```
<211> LENGTH: 21
<212> TYPE: DNA
<213> ORGANISM: Homo sapiens

<400> SEQUENCE: 23
ccatggaaac agttgatcct g                                              21

<210> SEQ ID NO 24
<211> LENGTH: 19
<212> TYPE: DNA
<213> ORGANISM: Homo sapiens

<400> SEQUENCE: 24
gctgttgctg ggttctttg                                                 19

<210> SEQ ID NO 25
<211> LENGTH: 20
<212> TYPE: DNA
<213> ORGANISM: Homo sapiens

<400> SEQUENCE: 25
attttgtgcg gtcgctctac                                                20

<210> SEQ ID NO 26
<211> LENGTH: 20
<212> TYPE: DNA
<213> ORGANISM: Homo sapiens

<400> SEQUENCE: 26
tccccattac ttccggtatc                                                20

<210> SEQ ID NO 27
<211> LENGTH: 20
<212> TYPE: DNA
<213> ORGANISM: Homo sapiens

<400> SEQUENCE: 27
catgcgtttc ttccactgag                                                20

<210> SEQ ID NO 28
<211> LENGTH: 20
<212> TYPE: DNA
<213> ORGANISM: Homo sapiens

<400> SEQUENCE: 28
catcggcact gcaaatactg                                                20
```